US008852408B2

(12) United States Patent
Chey et al.

(10) Patent No.: US 8,852,408 B2
(45) Date of Patent: Oct. 7, 2014

(54) ELECTROCHEMICAL LIQUID CELL APPARATUS

(75) Inventors: S. Jay Chey, Ossining, NY (US); Mark den Heijer, Dordrecht (NL); Aparna Prabhakar, White Plains, NY (US); Frances M. Ross, Ossining, NY (US); Ranjani Sirdeshmukh, Hastings on Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 949 days.

(21) Appl. No.: 12/432,037

(22) Filed: Apr. 29, 2009

(65) Prior Publication Data

US 2010/0276277 A1    Nov. 4, 2010

(51) Int. Cl.
    *C25B 9/00*     (2006.01)
    *C25B 9/06*     (2006.01)
    *C25B 9/12*     (2006.01)
    *C25B 1/04*     (2006.01)
    *G01N 27/416*     (2006.01)

(52) U.S. Cl.
    CPC ............................. *G01N 27/416* (2013.01)
    USPC ............................. 204/242; 204/193; 204/194

(58) Field of Classification Search
    CPC .............. C25B 9/06; C25B 9/00; C25B 1/04; C25B 9/12
    USPC .......................................... 204/242, 193, 194
    See application file for complete search history.

(56) References Cited

U.S. PATENT DOCUMENTS

| | | | | |
|---|---|---|---|---|
| 4,857,166 A | * | 8/1989 | Kotani | 204/435 |
| 6,631,022 B1 | * | 10/2003 | Kihira et al. | 359/265 |
| 2004/0194295 A1 | | 10/2004 | Green | |
| 2006/0124459 A1 | * | 6/2006 | Strand et al. | 204/450 |

OTHER PUBLICATIONS

E.P. Butler, et al., "Wet Cell Microscopy", Dynamic Experiments in the Electron Microscope—Practical Methods in Electron Microscopy, pp. 309-355, North Holland, 1981.

Hummingbird Scientific Data sheet, "TEM Holder for in Situ Fluid Experiments", Model FH-2000-TEM.

(Continued)

*Primary Examiner* — Zulmariam Mendez
(74) *Attorney, Agent, or Firm* — Louis J. Percello; Ryan, Mason & Lewis, LLP

(57) ABSTRACT

An electrochemical cell apparatus is disclosed where the cell has a chamber for containing an electrolyte. The chamber is situated between a bottom and a top substrate. One or more bottom windows are in the bottom substrate and one or more top windows are in the top substrate. Each window has a window cover facing the chamber. The top window and bottom window each have a portion in alignment so that an electron beam passes through both respective portions. A spacer is deposited between the top and bottom substrate and forming walls surrounding the chamber. Two or more electrodes, each having an interior portion that is within the chamber and electrically continuous with an exterior portion external to the chamber, are located on the chamber side of the bottom substrate.

10 Claims, 5 Drawing Sheets

(56) References Cited

OTHER PUBLICATIONS

M.J. Williamson, et al., "Dynamic Microscopy of Nanoscale Cluster Growth at the Solid-Liquid Interface", Nature Materials, pp. 532-536 and supplementary information, Aug. 2003, vol. 2, Nature Publishing Group.

Aleksander Radisic, et al., "Quantifying Electrochemical Nucleation and Growth of Nanoscale Clusters Using Real-Time Kinetic Data", Nov. 3, 2005, Revised Dec. 19, 2005, Nano Letters 2006, pp. 238-242, vol. 6, No. 2, American Chemical Society.

M.J. Williamson et al., "Dynamic Microscopy of Nanoscale Cluster Growth at the Solid-Liquid Interface," Nature Materials, Nature Publishing Group, 2003, ppl. 532-537, vol. 2.

P. Kim et al., "An Electrochemical Interface for Integrated Biosensors," IEEE Int. Conf. on Sensors, 2003, pp. 1036-1040.

International Search Report and the Written Opinion of the International Searching Authority, dated Jun. 29, 2010 for PCT/US10/32535.

\* cited by examiner

ELECTROCHEMICAL LIQUID CELL APPARATUS

FIELD OF THE INVENTION

The present invention is an electrochemical liquid cell apparatus. More specifically, the invention relates to an electrochemical liquid cell that can be used with a transmission electron microscope (TEM) to examine, evaluate, study, improve, and use electrochemical reactions, for example in the design and manufacture of integrated circuits.

BACKGROUND

The transmission electron microscope (TEM) has been used to examine solid materials since its invention in the 1940s. But liquid materials are much harder to examine. This is because the interior of the TEM is maintained at a high vacuum and most liquids, especially water-based solutions, would quickly evaporate into the vacuum before observations could be made.

"Liquid cells" are used in the prior art with TEM to examine electrochemical and other reactions in liquids. One such electrochemical cell (liquid cell), shown in FIG. 1, was designed, developed, and built at IBM's T. J. Watson Research Center and has proven successful in observing electrochemical reactions that take place in water-based solutions. Prior art cell design and some of the results obtained using such prior art are described in the following references, which are herein incorporated by reference in their entirety:
(1) M. J. Williamson, R. M. Tromp, P. M. Vereecken, R. Hull and F. M. Ross, Dynamic electron microscopy in liquid environments, Nature Materials 2, 532-536 (2003).
(2) A. Radisic, P. M. Vereecken, J. B. Hannon, P. C. Searson and F. M. Ross, Quantifying electrochemical nucleation and growth mechanisms from real-time kinetic data. Nano Letters 6, 238-242 (2006).
(3) E. P. Butler and K. F. Hale, *Dynamic Experiments in the Electron Microscope*. Elsevier (1981).
(4) Hummingbird Scientific, WA; http://www.hummingbird-scientific.com/PdfFiles/LiquidCellHolder.pdf Refer to the prior art electrochemical cell 100 shown in FIG. 1 in an isometric view and FIG. 2 shown in cross section 200.

The basic electrochemical cell design 100 consists of two silicon wafers, a bottom substrate 105 and a top substrate 115. A thin bottom insulator 108 (preferably made from a layer of silicon nitride, SiN, or other material such as silicon carbide) covers the bottom substrate chamber side 106 and a top insulator 111 covers the top substrate chamber side 116. Small areas of the two wafers are etched to remove the substrate but leave the insulator 108 and 111, thereby forming the top window 135 and bottom window 140; the bottom 108 and top 111 insulators form a cover over the bottom 140 and top 135 windows. The bottom substrate 105 has a backside 118 and the top substrate 115 has a backside 117. Both backsides (117 and 118) are opposite the respective chamber sides (106, 116). A spacer 107 is patterned on the bottom insulator 108. The spacer 107 is preferably in the shape of a rectangular outline surrounding the window, and is made from a material such as silicon dioxide. The wafers are then glued chamber side to chamber side so that the top window 135 and bottom window 140 are aligned, 197, and the spacer layer keeps them a fixed distance apart. This alignment allows the electron beam path 198 to pass through the top 135 and bottom 140 windows so that an image can be formed from transmitted electrons through the path 198 onto a detector/camera (not shown). The liquid/electrolyte under study 190 is introduced between the two substrates (105, 115) to form a thin layer, using a syringe to inject it (see below). If the two windows (135, 140) and the liquid layer, i.e., layer of electrolyte between the windows (135, 140) are thin enough for electrons from the TEM to pass through them, then the liquid and windows can be examined successfully in the TEM. The idea of encapsulating a liquid/electrolyte between SiN windows is well known.

In order to allow the liquid to be introduced easily, additional components of the cell were added to this original design. Thus, the complete design also includes features such as two tanks 125 to contain reservoirs 120 of the liquid 190, and two lids 130 to seal up the tanks. These components are attached to each other using glue. Apertures are placed in the top substrate 115 so that the electrolyte 190 in the tanks 125 and the space between the top 135 and bottom 140 windows is in fluid communication.

In addition, to allow electrochemical reactions to be observed two or three electrodes are required (160, 170, 180) which must be inserted into or to be in contact with the liquid. Each electrode must have part in contact with the liquid and part outside to allow electrochemical measurements to be made by connecting an external current or voltage source. The cell design shown in FIG. 1 gives one original method by which these electrodes were introduced. One electrode (the working electrode internal contact 155) is patterned so that part of it overlaps the bottom window 140. It is connected electrically outside the cell by patterning it over a via (hole) 109 that had been etched through the insulator 108 in a previous processing step, and by patterning a contact pad, the working electrode external contact 145 over a similar via near the edge of the cell. Electrical contact thus took place from the internal contact 155, through the Si wafer 150, out to the external contact 145. This allowed the external electrical contact 145 in the prior art to be outside the spacer 107. The other two electrodes, the reference electrode 170 and the counter electrode 180, were made of thin wires inserted manually into the cell through the topmost glue layer 181.

The cells built using this design were successful, but had yield problems that were associated with the design of the electrodes. The two electrodes made of wire 170 and 180 had to be placed manually and the caused leaks in the glue layer 181 between the lid 130 and the tanks 125 allowing the liquid to escape before the cell could be used. Even more significantly, the fabrication of the vias 109 and the patterning of the working electrode (both the internal 155 and external 145 contacts) were difficult. This was due to problems associated with the electrical connection between the electrode metal and the silicon wafer. In the prior art, the electrical current passed from an electrical source to the external electrode contact 145 and then through the bottom substrate 150 before flowing through the internal contact 155 and eventually to the electrolyte 190. The exposed substrate surface does not make a reliable contact with metal contacts such as 145 and 155 probably due to oxidation of the silicon, causing a high resistance between the contacts 145 and/or 155 and the bottom substrate 150 that inhibited current flow to the electrolyte 190. The poor and unreliable electrical contact between the two parts of the working electrode resulted in a low yield of working cell substrates, and the performance of each electrode had to be tested by making individual measurements which increased the process time drastically.

SUMMARY OF INVENTION

The present invention is an electrochemical cell apparatus. The cell has a chamber for containing an electrolyte. The chamber is situated between a bottom and top substrate. One or more bottom windows are in the bottom substrate. Each bottom window has a bottom window cover which is part of a continuous insulator over the surface of the bottom substrate. One or more top windows are in the top substrate. Each top window has a top window cover, part of a similar insulator over the top substrate. The top window and bottom window each have a portion in alignment so that an electron beam passes through both respective portions. A spacer is deposited between the top and bottom substrate forming walls surrounding the chamber. Two or more electrodes, each having an interior portion that is within the chamber and electrically continuous with an exterior portion external to the chamber, are located on the chamber side of the bottom or top substrate.

DETAILED DESCRIPTION OF A PREFERRED EMBODIMENT

Figure 1:
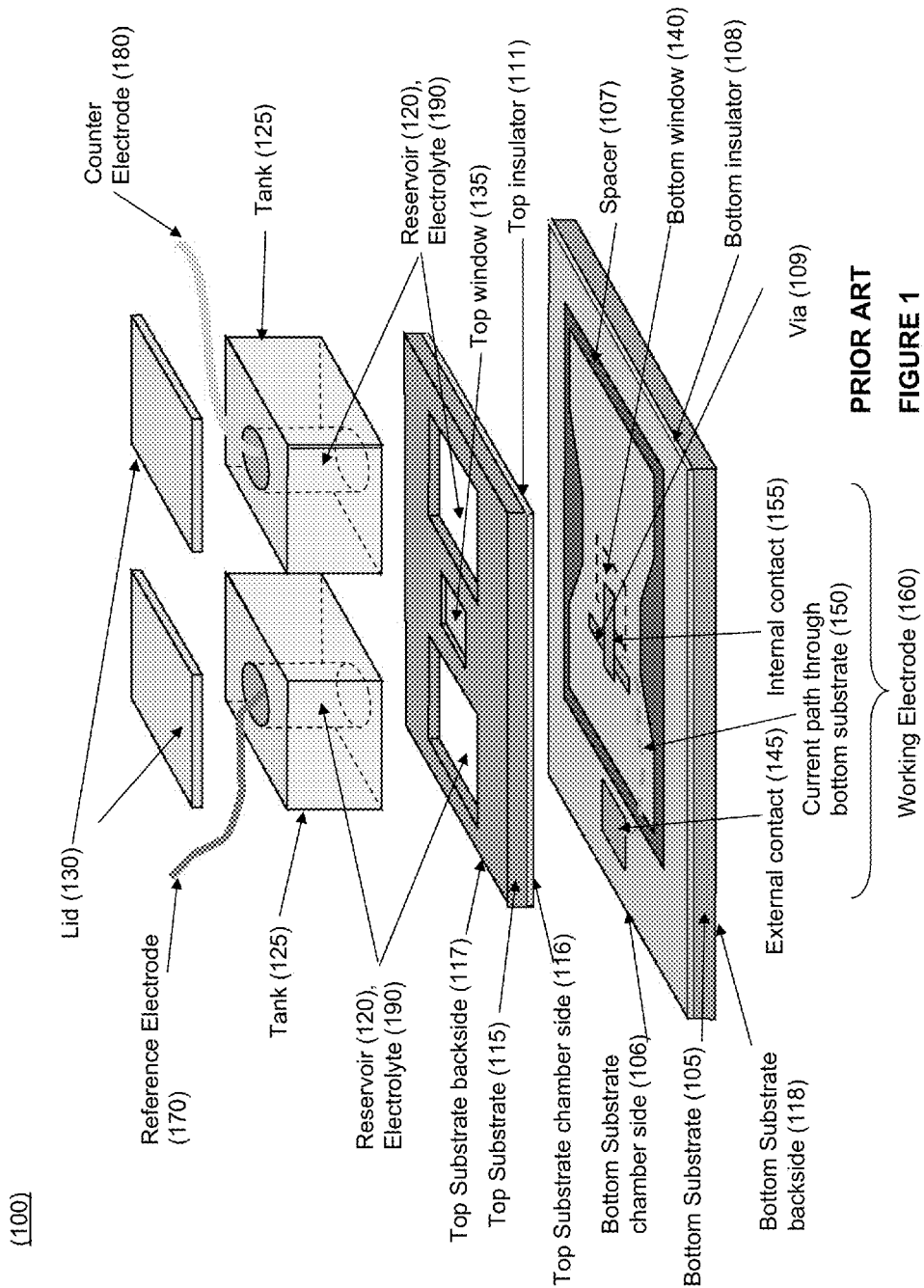
FIG. 1 is a block diagram of a prior art liquid electrochemical cell in isometric view.
Figure 2:
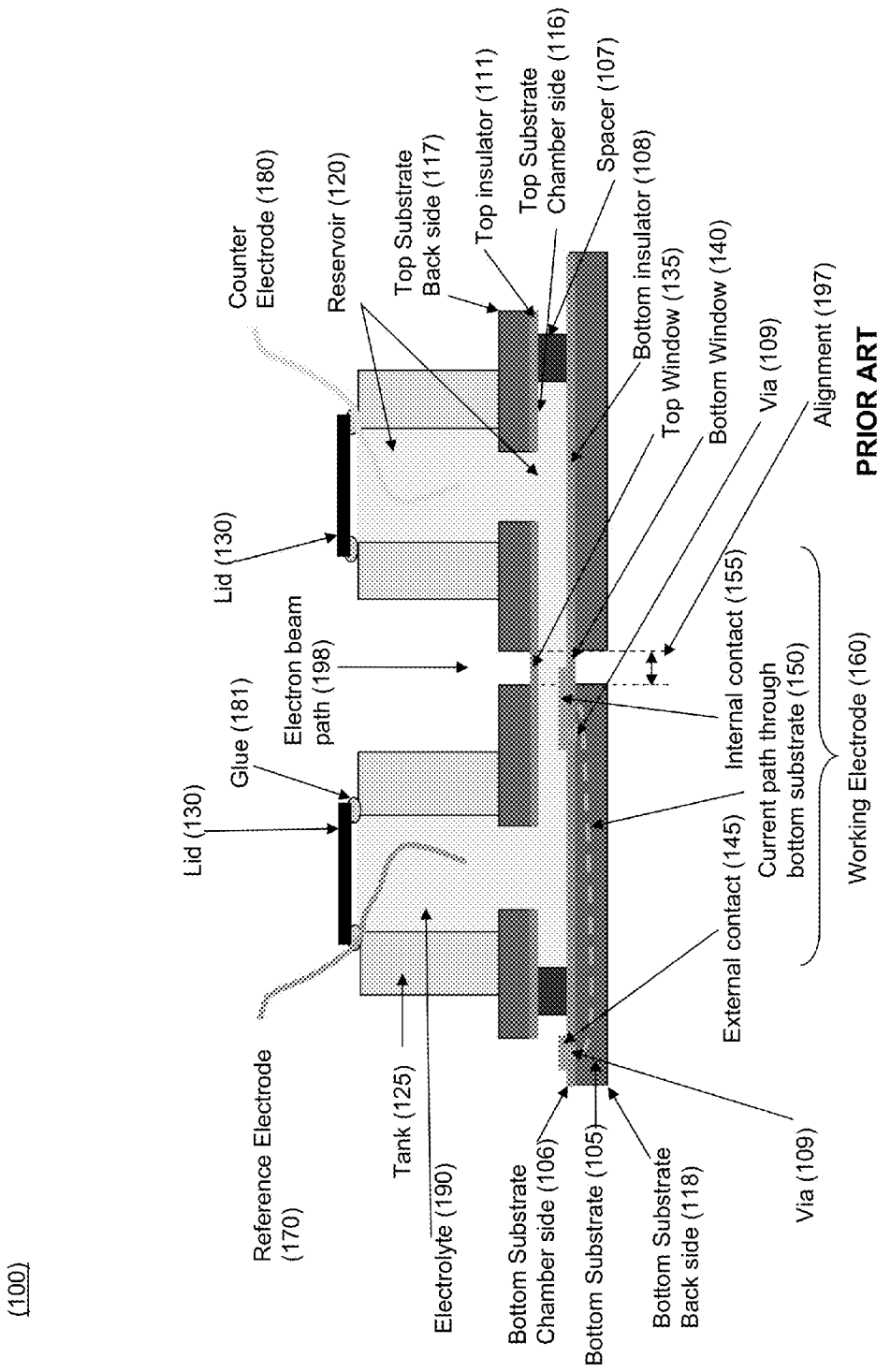
FIG. 2 is a cross sectional view of a prior art liquid electrochemical cell.

The present invention provides an improved electrochemical cell apparatus with improved electrode placement and connection. In one preferred embodiment, the cell is used for in situ transmission electron microscopy. Instead of using two wires for the counter and reference electrodes 180 and 170 and using internal 155 and external 145 contacts connected 150 through the bottom substrate 105 for the working electrode 160, at least one electrode and its electrical connection to the outside is a continuous metal strip patterned on one side of the insulator 108.

Figure 3:
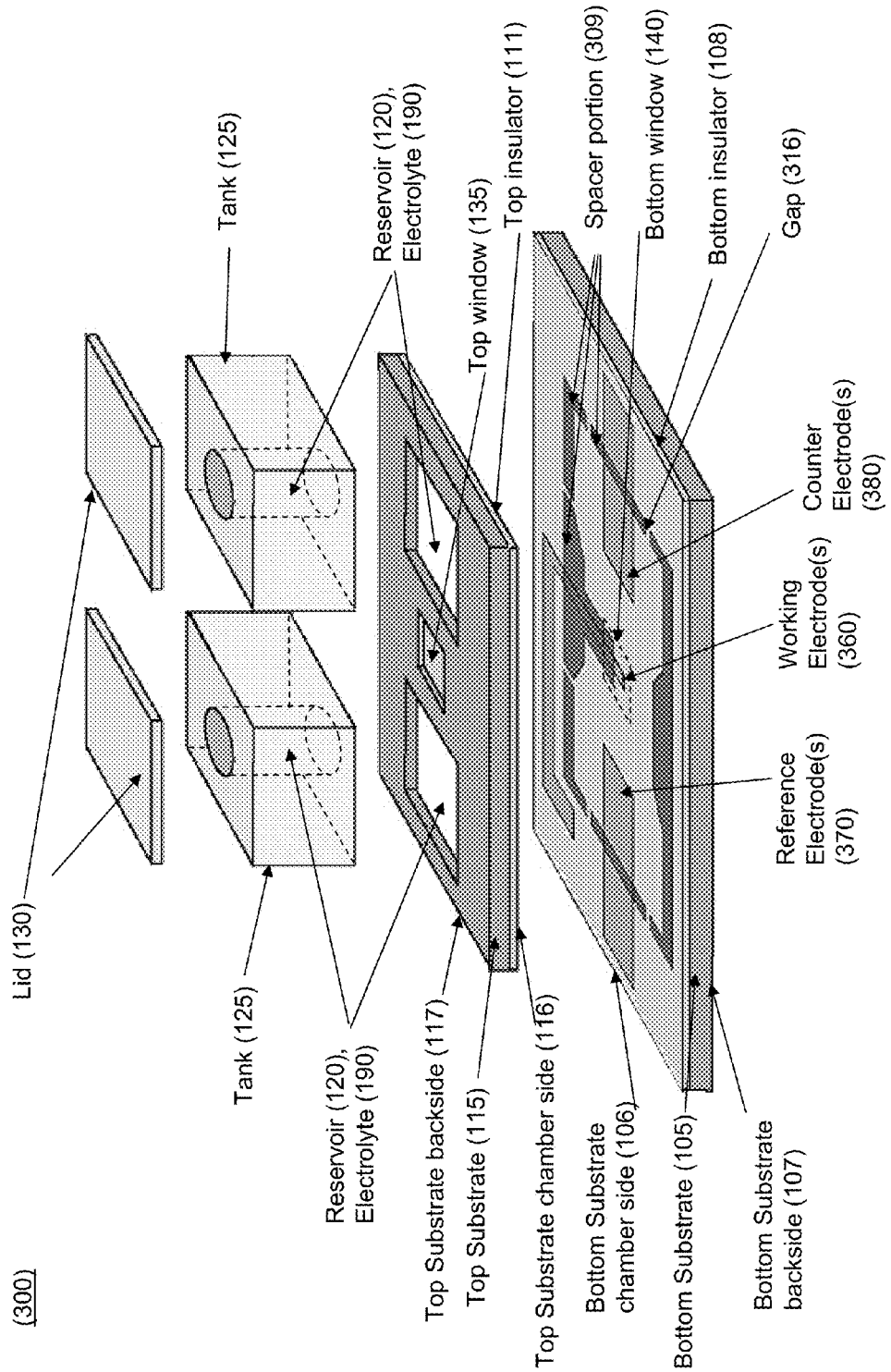
FIG. 3 is a block diagram of one preferred embodiment of the present invention, an electrochemical cell, in isometric view.
Figure 4:
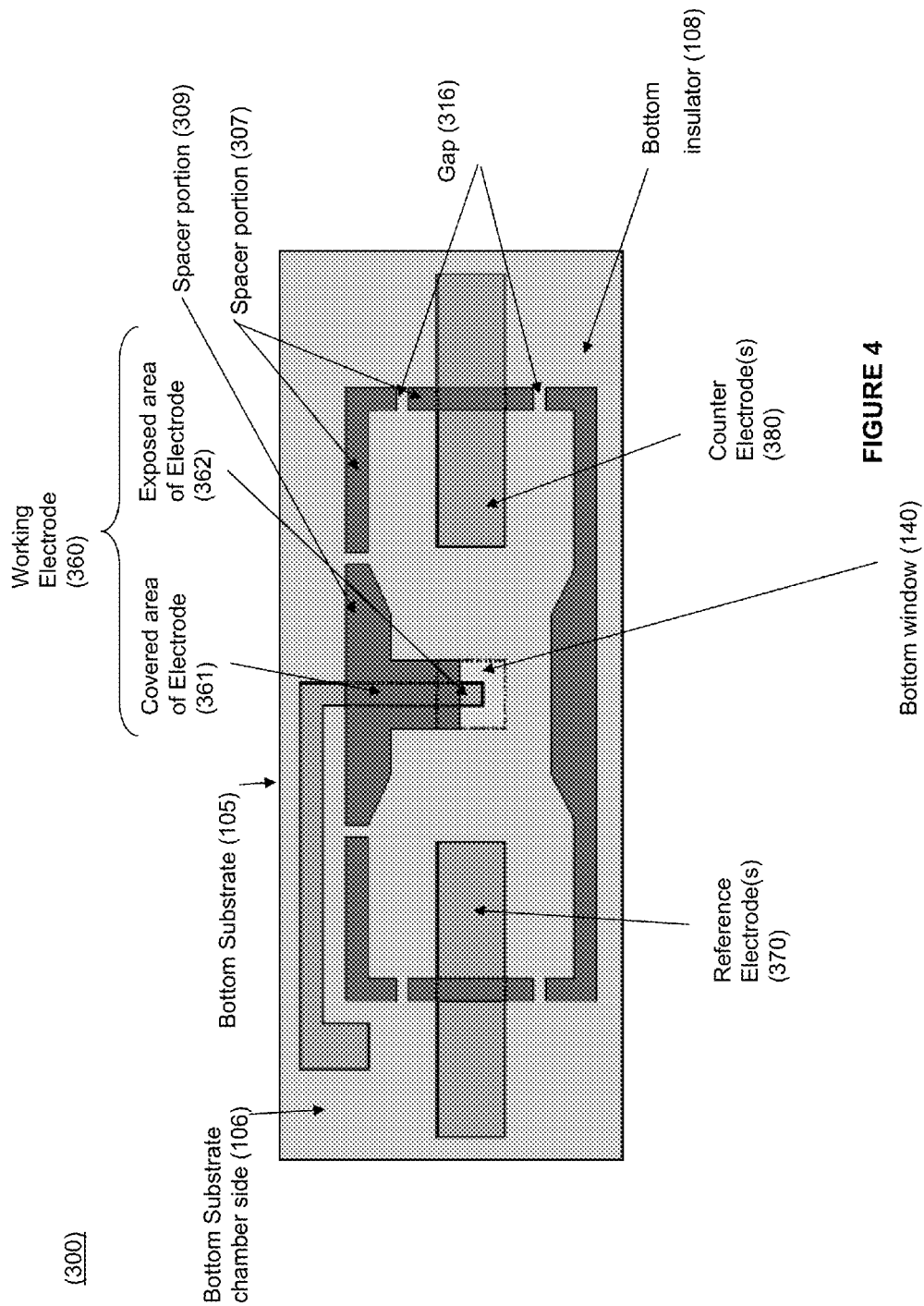
FIG. 4 is a top view of the bottom substrate of one preferred embodiment of the present invention, an electrochemical cell.
Figure 5:
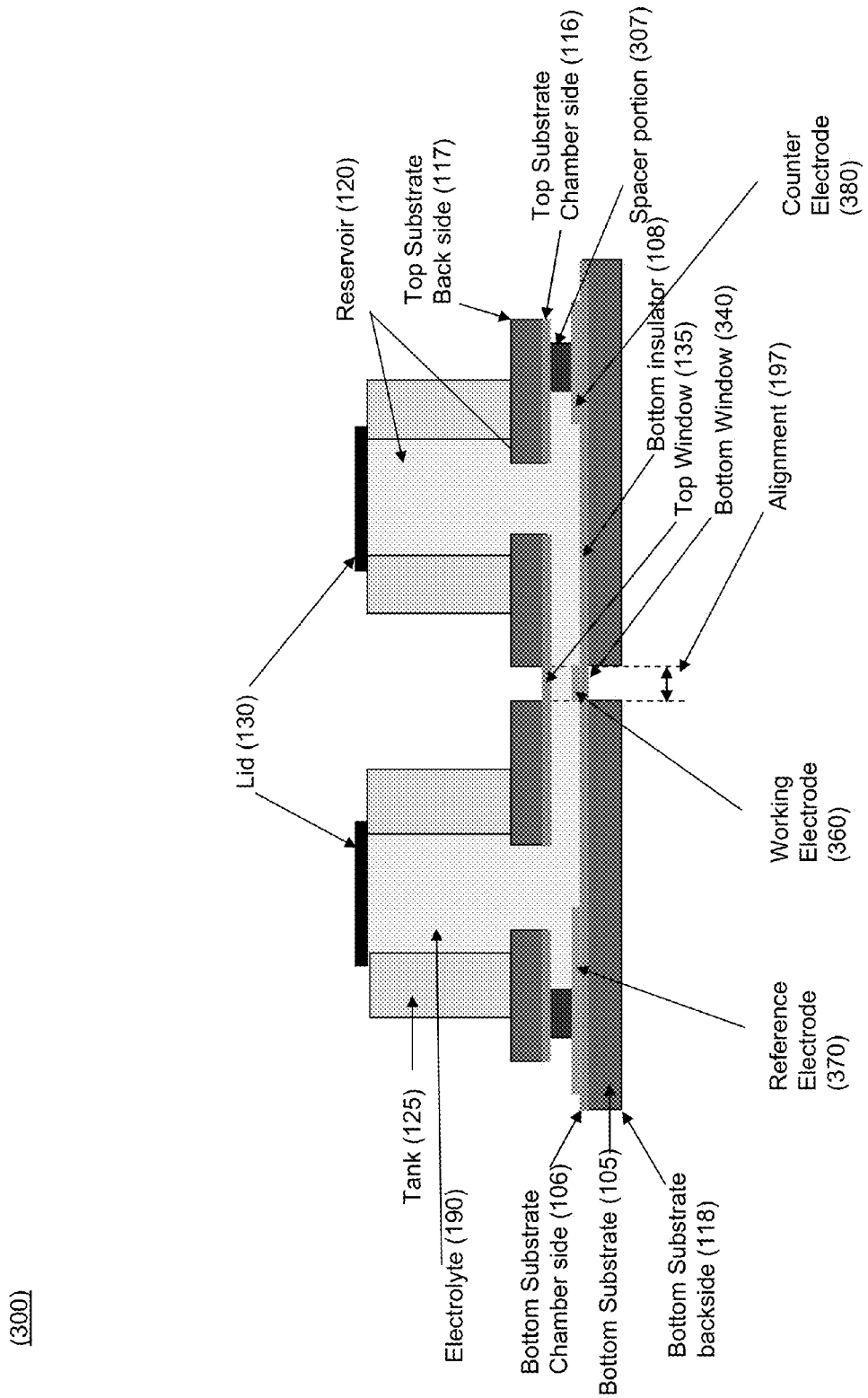
FIG. 5 is a cross sectional view of one preferred embodiment of the present invention, an electrochemical cell.

FIG. 3 is a block diagram showing one preferred design 300 in which all three electrodes are patterned onto the bottom insulator 108 of a bottom substrate 105. Refer also to FIGS. 4 and 5. Reference numbers that are the same in the Figures represent the same component.

The electrodes (360, 370, 380) are continuous metal strips which extend from the inside to the outside of the cell.

Using this design, the fabrication of the working electrode 360 is improved. The prior art processing steps by which the via 109 is patterned and etched, and the processing step by which the working electrode external and internal contacts 145 and 155 are aligned with the via 109, are both avoided. The working electrode 360 has a better and more reliable electrical connection as the current does not have to pass through the bottom substrate 105 and across the interface between the bottom substrate 105 and the internal 155 and external 145 contacts.

Using this design, the area of the working electrode 360 that is exposed to the liquid/electrolyte 190 can be optimized, while still maintaining a good electrical connection outside the cell. To achieve this, in one embodiment (refer to FIG. 4), the working electrode is partially covered 361 with a spacer layer portion 309 and partially exposed 362 to the liquid/electrolyte 190. The spacer layer 309 electrically insulates the partially covered 361 portion of the working electrode 360 from the liquid 190. Therefore, using the structure of the present invention, the area of the partially exposed 362 portion of the working electrode 360 can be controlled lithographically to achieve an optimal area.

The exposed area of the working electrode 362 is important for several reasons. If the area is too large, then a large number of ions are removed from the liquid/electrolyte 190 during the electrochemical reaction. This will change the ion concentration in the electrolyte, especially because the total volume of electrolyte in the cell is small. On the other hand, the exposed area 362 can also be too small to allow adequate current flow.

The optimal area of the exposed area 362 depends on the following factors: the volume of the liquid 190 in the chamber reservoir 120; the type of electrolyte 190, e.g., which and how many ions (in a preferred embodiment, a metal cation); the material of the working electrode 360; and the value and rate of change of the electrical potential applied to the working electrode 360. A preferred area for the exposed portion 362 is between 1 square microns and 500 square microns. A more preferred range of the exposed portion 362 is between 10 square microns and 200 square microns.

Using this design, the reference electrode 370 and counter electrode 380 are improved also. The prior art fabrication steps of introducing the two wires 170 and 180 and sealing them, a leak-prone process, is avoided. Furthermore, the areas of the reference electrode 370 and counter electrode 380 exposed to the liquid/electrolyte are controlled lithographically rather than depending on the details of how the wire are placed in the liquid. A preferred area of the reference electrode 370 and counter electrode 380 is on the order of ten times greater than the exposed area of the working electrode 362, which was discussed above.

An additional advantage of the present design is that the reference 370 and counter 380 electrodes may be geometrically closer to the working electrode 360 than was possible in prior art using the inserted wires 170 and 180. In particular, a short distance between the reference electrode 370 and working electrode 360 allows the reference electrode to measure the potential on the working electrode more accurately, and therefore enables better electrochemical response from the cell. However, if the separation is too small, there is a possibility of an electrical short circuit between the electrodes if there are errors in lithography. A preferred separation between the reference electrode 370 and working electrode 360 is between 1 micron and 500 microns. A more preferred range is between 50 microns and 100 microns.

The distance between the counter electrode 380 and working electrode 360 is also important to the cell design. A larger distance is optimal to ensure even current flow to the working electrode. A preferred separation between the counter electrode 380 and working electrode 360 is between 500 microns and 2000 microns.

In order to avoid short circuits between the three electrodes (360, 370, 380), in one embodiment, gaps 316 in the spacer 307 are provided, dividing the spacer 307 into spacer portions 309. The gaps 316 avoid the possibility that the electrodes (360, 370, 380) will be electrically shorted if the spacer is electrically conductive. (A preferred choice for the spacer material is in fact electrically conducting, as it is silicon dioxide on a metal adhesion layer such as chromium.) However, if the gaps are too wide, it may be more difficult to seal the top substrate 115 to the bottom substrate 105. The optimal width of the gaps depends on the material and thickness of the spacer 307. A preferred gap width is between 10 microns and 100 microns.

Maybe this is a good place to note that there is another way to avoid a possible short circuit: that is to pattern all electrodes on the bottom piece and pattern the spacer layer on the top piece (or vice versa). If the two pieces are glued together the insulating side of the spacer layer (the SiN) is pushed against the electrodes which does not cause a short circuit.

In a preferred embodiment, it is important to keep the thickness of the electrodes (360, 370, 380) much less than the thickness of the spacer 307, to ensure flatness of the spacer layer where it passes over the electrodes. A preferred value of the thickness of the spacer 307 is between 200 nanometers and 500 nanometers and a preferred electrode thickness is between 10 nanometers and 200 nanometers.

The improvements discussed above allow the cell 300 to be fabricated with much higher yields. Extensive testing of cell components, necessary because of uncertainties in the quality of the electrical contact, is avoided in the present design. Furthermore the cell 300 can be operated more easily in the microscope and the data it provides is more representative of a large scale electrochemical process.

Alternative preferred embodiments of the present invention result when the structure is modified to allow different materials, numbers, and geometrical arrangements of the electrodes and one or more windows.

In the embodiment described here, three electrodes are formed of gold, which is a preferred material as it is inert and has a very low resistance. However, the use of the cell to examine electrochemical processes may require the use of a material other than gold for one or more of the electrodes. Two processes may be used to create a cell with electrodes made of a material other than gold. First, it is possible to deposit other materials (e.g. any conductive material, preferably copper, nickel, or silver), using evaporation or sputtering, onto the gold or in place of the gold to form any one or more of the three (or more) electrodes. A second, more convenient process is to deposit other materials (e.g. any conductive material, preferably copper, nickel, or silver) electrochemically onto any of the three electrodes before assembling the cell.

In another embodiment, there may be two, four or another number of electrodes. In one embodiment, two electrodes may be patterned onto the bottom insulator of a bottom substrate but with both electrodes patterned so that part of them overlap the bottom window 340. These electrodes may be in close proximity, with constraints as described above, separated by a preferred distance of between 10 micrometers and 100 micrometers. In this embodiment, it is possible to apply a voltage between the two electrodes to study the behavior of charged or polar particles in an electric field.

In another embodiment, one electrode may be patterned onto the bottom insulator 108 of the bottom substrate 105 and a second electrode may be patterned onto the top insulator of a top substrate (not shown). In this embodiment the possibility of short circuits between the electrodes is minimized. Furthermore, by using such electrodes or by placing marks on the upper and lower windows, for example by lithography, the separation of the windows can be measured in situ by tilting the cell.

In another embodiment, four or more electrodes may be patterned. These electrodes may be made of different materials, or may have different areas or separations from other electrodes. By connecting the voltage or current source to different combinations of electrodes, different electrochemical experiments can be carried out in one cell.

The invention claimed is:

1. An electrochemical cell having a chamber for containing an electrolyte, the electrochemical cell further comprising:
   a bottom substrate having a bottom substrate chamber side and a bottom substrate back side;
   a top substrate having a top substrate chamber side and a top substrate back side;
   a chamber disposed between the top and bottom substrate and defined in part by the chamber sides of the top and bottom substrates;
   one or more bottom windows in the bottom substrate, the bottom window having a bottom window cover facing the chamber;
   one or more top windows in the top substrate, the top window having a top window cover facing the chamber, the top window and bottom window each having a portion in alignment so that an electron beam passes through both respective portions;
   a spacer deposited on the chamber side of the bottom substrate and forming walls surrounding the chamber; and
   two or more planar electrodes patterned on the chamber side of the bottom substrate, each planar electrode having a first portion that is disposed within a same interior region of the chamber and a second portion that is disposed external to the chamber and a third portion that is overlapped by a portion of the spacer forming said walls, wherein the first and second and third portions of each planar electrode are electrically continuous.

2. A cell, as in claim 1, where there are three electrodes, being a reference electrode, a working electrode, and a counter electrode.

3. A cell, as in claim 1, where there are more than three electrodes, three of which being electrically activated.

4. A cell, as in claim 1, where at least one of the electrodes is made of any one or more of the following materials: a metal, gold, copper, nickel, and silver.

5. A cell, as in claim 1, where at least one of the electrodes is made of a first material with a plated layer of a second material.

6. A cell, as in claim 1, where the spacer comprises two or more spacer portions, each spacer portion in contact with at most one of the electrodes, and where there is at least one gap between any two adjacent spacer portions to provide electrical isolation through the spacer between the electrodes.

7. A cell, as in claim 6, wherein the at least one gap is at least 1 micron.

8. A cell, as in claim 1, where a portion of the spacer overlaps over a portion of at least one of the electrodes to define an exposed area of the electrode within said interior region of the chamber.

9. A cell, as in claim 1, where the thickness of the spacer is between 50 nanometers to 100 micrometers.

10. A cell, as in claim 1, where the spacer is made of a non conductive material.

* * * * *